United States Patent [19]

Nayler

[11] Patent Number: 4,460,582
[45] Date of Patent: Jul. 17, 1984

[54] 3-CARBOXYBENZYL CEPHEMS

[75] Inventor: John H. C. Nayler, Dorking, England

[73] Assignee: Beecham Group P.L.C., England

[21] Appl. No.: 353,025

[22] Filed: Mar. 1, 1982

[30] Foreign Application Priority Data

Mar. 5, 1981 [GB] United Kingdom ............... 8106891

[51] Int. Cl.$^3$ ............... A61K 31/545; C07D 501/24
[52] U.S. Cl. ........................... 424/246; 544/16; 544/22; 544/23
[58] Field of Search .................. 544/22; 424/246

[56] References Cited

U.S. PATENT DOCUMENTS 3,932,465  1/1976  Peter et al. ..................... 544/16
4,264,595  4/1981  Numata et al. .................. 544/22
4,298,606  11/1981 Ochiai et al. ................... 424/246

FOREIGN PATENT DOCUMENTS 2089339A  6/1982  United Kingdom .

Primary Examiner—Paul M. Coughlan, Jr.
Attorney, Agent, or Firm—Jacobs & Jacobs

[57] ABSTRACT

The present invention provides a compound of the formula (I):

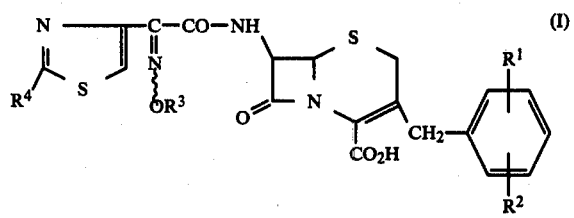

and pharmaceutically acceptable salts and in-vivo hydrolysable esters thereof wherein $R^1$ is carboxy, $R^2$ is hydrogen or carboxy, $R^3$ is hydrogen, acyl, $C_{1-6}$ akyl or $C_{2-6}$ alkenyl, any of such $R^3$ groups being optionally substituted, and $R^4$ is an amino or protected amino group.

Processes for the preparation of these compounds are described as is their use in the treatment of bacterial infection.

24 Claims, No Drawings

3-CARBOXYBENZYL CEPHEMS

This invention relates to novel β-lactam derivatives and in particular to 3-carboxybenzyl cephem derivatives. This invention further relates to processes for their preparation and to compositions containing them. These derivatives are of use in the treatment of bacterial infection.

The present invention provides a compound of the formula (I):

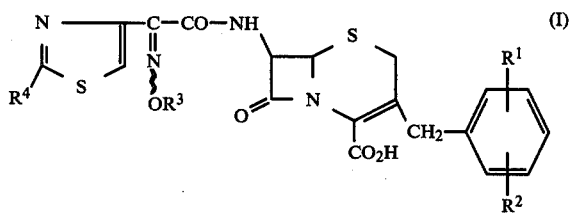

and pharmaceutically acceptable salts and in-vivo hydrolysable esters of any carboxy group wherein $R^1$ is carboxy, $R^2$ is hydrogen or carboxy, $R^3$ is hydrogen, acyl, $C_{1-6}$ alkyl or $C_{2-6}$ alkenyl, any of such $R^3$ groups being optionally substituted, and $R^4$ is an amino or protected amino group.

The group $R^1$ is preferably in the form of carboxy group. In an alternative aspect $R^1$ is a salified carboxy group.

Suitably $R^2$ is a hydrogen atom. Suitably also $R^2$ is a carboxy group which optionally may be salified.

The substituent $R^1$ may be located at the ortho, meta or para-position of the phenyl ring. Of these it is preferred that $R^1$ is in the para-position.

Suitably $R^3$ is hydrogen, acyl, $C_{1-6}$ alkyl or $C_{2-6}$ alkenyl. When used herein the term "acyl" includes carboxylic acyl such as $C_{1-6}$ alkanoyl, for example formyl, acetyl and propionyl; $C_{1-6}$ alkoxycarbonyl, for example methoxycarbonyl and ethoxycarbonyl; arylcarbonyl such as benzoyl and naphthoyl; aryl ($C_{1-6}$) alkanoyl such as phenylacetyl; and aryl ($C_{1-6}$) alkoxycarbonyl such as benzyloxycarbonyl; "acyl" also includes sulphonic acyl such as $C_{1-6}$ alkanesulphonyl for example methanesulphonyl and ethanesulphonyl, and arylsulphonyl for example benzenesulphonyl and toluenesulphonyl; "acyl" further includes carbamoyl, for example $C_{1-6}$ alkyl carbamoyl such as methylcarbamoyl, arylcarbamoyl such as phenylcarbamoyl, aryl ($C_{1-6}$) alkylcarbamoyl such as benzylcarbamoyl, and $C_{1-6}$ alkanoylcarbamoyl such as formylcarbamoyl and acetylcarbamoyl; "acyl" also includes phosphoric acyl such as ($C_{1-6}$ alkoxy)$_2$P(=O)O— for example $(CH_3O)_2P(=O)O$—.

Suitable optional substituents for the group $R^3$ include chloro, bromo, fluoro, hydroxy, carboxy, $C_{1-6}$ alkoxy, acyl, $C_{1-6}$ alkyl and aryl.

When used herein "aryl" includes phenyl, naphthyl, thienyl, pyridyl, pyrrolyl, indolyl and furyl.

More suitably $R^3$ is hydrogen, methyl, ethyl, propyl, butyl, formyl, acetyl, methoxycarbonyl, ethenyl, methanesulphonyl, carboxymethyl, carboxyethyl and 2-carboxyprop-2-yl.

Preferably $R^3$ is a hydrogen atom. Preferably $R^3$ is a methyl group.

The group $R^4$ is an amino group or a protected amino group. The amino group may be protected in conventional manner for example as an acylamino group such as methoxycarbonyl, or as a alkylidene such as benzylidene, or as an aralkylamino group such as trityl, benzyl or benzhydryl.

Preferably $R^4$ is an amino group.

It is to be realised that the compounds of this invention exist either in the syn-form (II) or in the anti-form (III) or as mixtures thereof:

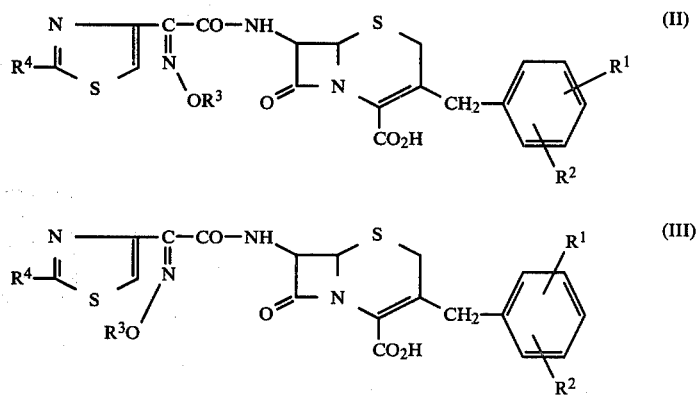

In general the syn-form is preferred.

Compounds of this invention wherein $R^4$ is an amino group may exist in the form of a tautomeric mixture which is represented by the partial structures (IV) and (V):

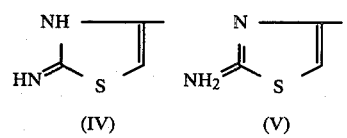

A preferred sub-group of compounds is that of the formula (VI):

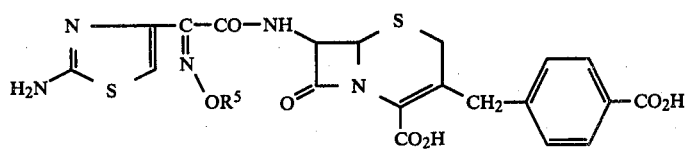

and pharmaceutically acceptable salts thereof wherein $R^5$ is a hydrogen atom or a $C_{1-4}$ alkyl group optionally substituted by carboxy.

Particular compounds of this invention include:
(6R,7R)-3-(4-carboxybenzyl)-7-[2,Z-methoxyimino-2-(2-aminothiazol-4-yl)-acetamido]-ceph-3-em-4-carboxylic acid,
(6R,7R)-3-(4-carboxybenzyl)-7-[2-Z-ethoxyimino-2-(2-aminothiazol-4-yl)-acetamido]-ceph-3-em-4-carboxylic acid, and
(6R,7R)-3-(4-carboxybenxyl)-7-[2,Z-(2-carboxyprop-2-oxyimino)-2-(2-aminothiazol-4-yl)-acetamido]-ceph-3-em-4-carboxylic acid, and salts thereof.

Suitable pharmaceutically acceptable salts include acid addition salts of the compounds of this invention which contain amino groups, as well as salts of the various carboxy groups. Such salts include sodium, potassium, magnesium, calcium, aluminium, ammonium and substituted ammonium salts. Of these the sodium and potassium salts are preferred.

Pharmaceutically acceptable in-vivo hydrolysable esters are those esters which hydrolyse in the human body to produce the parent acid or its salt. Such esters may be identified by administration to a test animal such as a rat or mouse by intravenous administration and thereafter examining the test animal's body fluids for the presence of the compound of the formula (I) or its salt. Suitable esters of this type are those conventionally known in the art and include those of sub-formula (a):

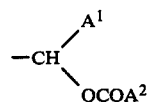

wherein $A^1$ is a hydrogen atom or a methyl group, and $A^2$ is a $C_{1-4}$ alkyl, phenyl or $C_{1-4}$ alkoxy group or $A^1$ is joined to $A^2$ to form a phthalidyl, dimethylphthalidyl or dimethoxyphthalidyl group.

Preferred groups of the sub-formula (a) include the acetoxymethyl, pivaloyloxymethyl, α-ethoxycarbonyloxymethyl and phthalidyl groups.

In another aspect the present invention provides a pharmaceutical composition which comprises a compound of the formula (I) or a pharmaceutically acceptable salt or in-vivo hydrolysable ester thereof and a pharmaceutically acceptable carrier.

The compositions of this invention may be prepared by conventional methods of preparing antibiotic compositions and in conventional manner may be adapted for oral, topical or parenteral administration.

In a preferred aspect the compositions of this invention are in the form of a unit-dose composition adapted for administration by injection.

Unit dose forms according to this invention will normally contain from 100 mg to 4 g of a compound of this invention, more usually from 125 mg to 1 g and normally from 200 mg to 600 mg. Such compositions may be administered from 1 to 6 times daily, but a preferred aspect of the compounds of this invention is that they have a tendency to possess prolonged blood levels after administration. These blood levels are such that the compositions of this invention generally need to be administered only 2 to 3 times daily.

The compositions of this invention may be used to treat bacterial infection in animals such as mammals including humans, for example infections of the respiratory tract, urinary tract or soft tissues, or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato starch or polyvinylpolypyrrolidone, magnesium stearate or sodium lauryl sulphate.

In a further aspect the present invention provides a process for the preparation of the compounds of the formula (I) or pharmaceutically acceptable salts or in-vivo hydrolysable esters thereof which process comprises the reaction of a compound of the formula (VII) or a derivative thereof which permits N-acylation to take place:

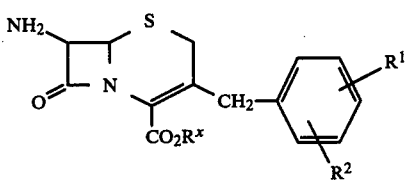

wherein $R^1$ and $R^2$ are as defined in relation to formula (I) and where any carboxy group may be optionally protected as a carboxy-blocking group and $R^x$ is a hydrogen atom or a carboxy-blocking group, with an N-acylating derivative of a carboxylic acid of the formula (VIII):

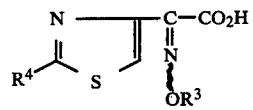

wherein $R^3$ and $R^4$ are as defined in relation to formula (I) and any reactive group is optionally protected, and thereafter if necessary:
(i) removing any protecting group,
(ii) converting the product into a pharmaceutically acceptable salt or in-vivo hydrolysable ester.

Suitable groups which permit acylation to take place and which are optionally present on the amino group of the starting material of the formula (VII) include N-silyl, N-stannyl and N-phosphorus groups, for example trialkylsilyl groups such as trimethylsilyl, trialkyltin groups such as tri-n-butyltin, groups of formula —P.-$R^aR^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being $-P(OC_2H_5)_2$, $-P(C_2H_5)_2$, and 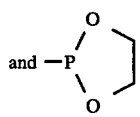

Suitable carboxyl-blocking derivatives for the groups $R^1$, $R^2$ and $-CO_2R^x$ in formula (VII) include salts, ester, and anhydride derivatives of the carboxylic acid. The derivative is preferably one which may readily be cleaved at a later stage of the reaction. Suitable salts include inorganic salts, for example alkali metal salts such as the sodium salt, tertiary amine salts, such as those with tri-lower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula $-N=CHR°$ where $R°$ is aryl or heterocyclic, or an in vivo hydrolysable ester radical such as defined above.

The carboxyl group may be regenerated from any of the above esters by usual methods appropriate to the particular group, for example, acid—and base—catalysed hydrolysis, or by enzymically—catalysed hydrolysis, or by hydrogenation.

A reactive N-acylating derivative of the acid (VIII) is employed in the above process. Suitable N-acylating derivatives include an acid halide, preferably the acid chloride or bromide. Acylation with an acid halide may be effected in the presence of an acid binding agent for example molecular sieve or a pyridine or a tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{1-6})$-1,2-alkylene oxide—such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (VIII) or a salt thereof with a halogenating (e.g. chlorinating or brominating) agent such as phosphorus pentachloride, thionyl chloride or oxalyl chloride.

Alternatively, the N-acylating derivative of the acid (VIII) may be a symmetrical or mixed anhydride. Suitable mixed anhydrides are alkoxyformic anhydrides, or anhydrides with, for example carbonic acid mono-esters, trimethyl acetic acid, thioacetic acid, diphenylacetic acid, benzoic acid, phosphorus acids (such as phosphoric or phosphorous acids, sulphuric acid or aliphatic or aromatic sulphonic acids such as p-toluenesulphonic acid). The mixed or symmetrical anhydrides may be generated using N-ethoxycarbonyl-2-ethoxyl-2-ethoxy-1,2-dihydroquinoline. When a symmetrical anhydride is employed, the reaction may be carried out in the presence of 2,6-lutidine as catalyst.

Alternative N-acylating derivatives of acid (VIII) are the acid azide, or activated esters such as esters with 2-mercaptothiazoline, 2-mercaptopyridine, cyanomethanol, p-nitrophenol, 2,4-dinitrophenol, thioalcohols such as thiophenol, methanethiol, ethanethiol and propanethiol, halophenols, including pentachlorophenol, monomethoxyphenol of 8-hydroxyquinoline, N-hydroxysuccinimide or 1-hydroxybenztriazole; or amides such as N-acylsaccharins or N-acylphthalimides; or an alkylidine iminoester prepared by reaction of the acid (VIII) with an oxime.

Other reactive N-acylating derivatives of the acid (VIII) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-$\gamma$-dimethylaminopropylcarbodiimide; a suitable carbonyl compound, for example N,N'-carbonyl- diimidazole or N,N'-carbonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3-C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan or tetrahydrofuran.

In a further aspect the present invention provides a process for the preparation of the compounds of the formula (I) which process comprises:

(a) treating a compound of the formula (IX):

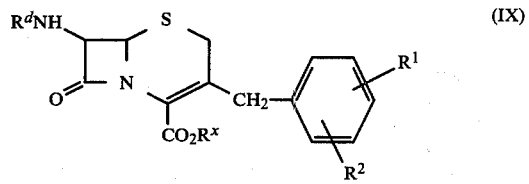

wherein $R^1$, $R^2$ and $R^x$ are as hereinbefore defined, and $R^d$ is an acyl group with an agent forming an imino halide;

(b) treating the imino halide with a compound to introduce a group $QR_f$ on the imino carbon atom, wherein Q is oxygen, sulphur or nitrogen and $R_f$ is an alkyl group of from 1 to 14 carbon atoms, to form an iminoether, iminothioether, or amidine (when Q is O, S, or N respectively);

(c) reacting with an N-acylating derivative of an acid of formula (VIII) above;

(d) treating with water; and (e) optionally removing any carboxyl-blocking groups $R^x$, and optionally removing any other protecting groups.

Preferably $R^d$ is a group of the sub-formula (b)–(e):

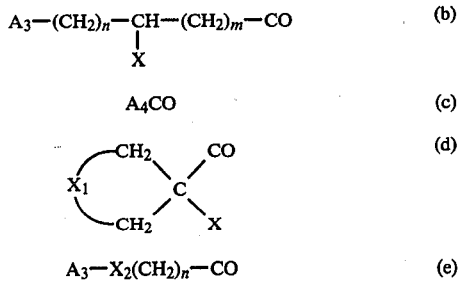

wherein n is 0, 1 or 2; m is 0, 1 or 2; $A_3$ is $C_{1-6}$ alkyl, $C_{3-6}$ cycloalkyl, cyclohexenyl, cyclohexadienyl, phenyl, substituted phenyl, thienyl or pyridyl group, X is a hydrogen or halogen atom, a free or esterified carboxy group, azido, tetrazolyl, hydroxy, acyloxy, amino, ureido, guanidino or acylureido group; $A_4$ is a 2,6-dimethoxyphenyl, 2-alkoxy-1-naphthyl, 3-aryl-4- or 5-isoxazolyl, or 3-aryl-5-methyl-4-isoxazolyl group; $X_1$ is a $CH_2OCH_2$, $CH_2SCH_2$ or $(CH_2)_n$ group wherein n is 0, 1 or 2; and $X_2$ is an oxygen or sulphur atom.

A suitable agent for preparing an imino halide is an acid halide in the presence of an acid binding agent such as a tertiary amine, e.g. pyridine, triethylamine, or N,N-dimethylaniline. Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from 0° C. to −30° C. when phosphorus pentachloride is employed. The amount of the tertiary amine is preferably 3–5 mols per mol of phosphorus pentachloride. It is also preferable to use the phosphorus halide in an amount slightly in excess of that of the starting material.

The resulting imino compounds are then treated to introduce a $—QR_f$ group onto the imino carbon atom. This is preferably effected by reacting the imino halide with a corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2-phenylethanol.

The reaction of the alcohol with the imino halide is preferably effected in the presence of an acid binding agent, such as a tertiary amine, preferably pyridine, and the reaction is usually carried out without isolating the imino halide from the reaction mixture.

Thereafter the imino compound is caused to react with an N-acylating derivative of an acid of formula (VIII). The comments made above concerning such N-acylating derivatives, and the conditions for carrying out acylations also apply in this case. In particular, the presence of a tertiary amine such as pyridine or N,N-dimethylaniline in the reaction system is preferred.

Finally, the product is treated with water. The water treatment may be conducted together with the isolation of the desired material. That is the reaction mixture may be added to water or a saturated aqueous solution of sodium chloride and then the aqueous layer formed is separated from the organic solvent layer.

The preparation of the compounds of the formula (VII) and (IX) are disclosed in British Patent Specification No. 1,505,345.

The compounds of the formula (VIII) are known in the art and may be produced by known procedures, procedures known per se or procedures analogous thereto.

The following Examples illustrate the invention.

EXAMPLE 1

(6R,7R) t-Butyl 3-(4-Carboxybenzyl)-7-[2,Z-methoxyimino-2-(2-triphenylmethylaminothiazol-4-yl)acetamido]ceph-3-em-4-carboxylate (2)

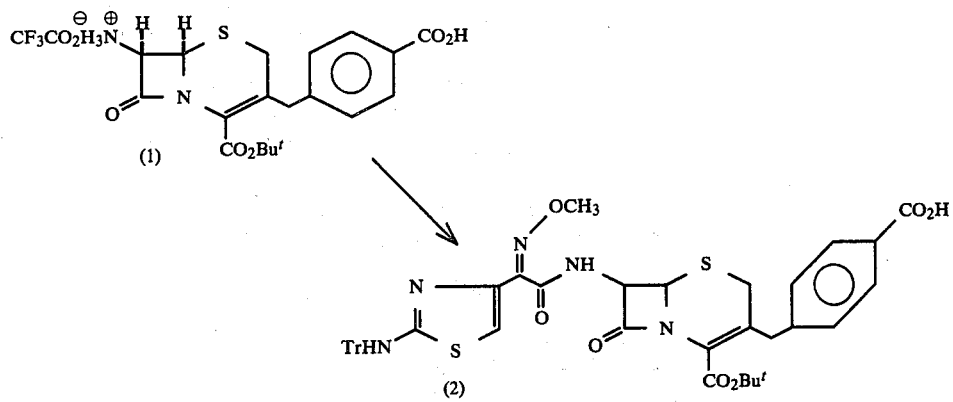

2,Z-Methoxyimino-2-(2-triphenylmethylaminothiazol-4-yl)acetic (222 mg; 0.5 mmol) in dry methylene chloride (MDC) (3 ml) at −10° C. was treated with triethylamine (51 mg; 0.5 mmol) followed by phosphorus pentachloride (104 mg; 0.5 mmol) and stirred at −10°/0° C. for 1 hour. The solution was concentrated in vacuo and the residue taken up in dry tetrahydrofuran (THF) (3 ml) and added to solution of (6R,7R) t-butyl 3-(4-carboxybenzyl)-7aminoceph-3-em-4-carboxylate trifluoroacetic acid salt (1; 336 mg; equivalent to 0.5 mmol at an assumed purity of 75%) containing triethylamine (152 mg; 1.5 mmol) in dry THF (3 ml) at 0° C. with stirring. The solution was allowed to warm to room temperature and after 1 hour the solvent was evaporated in vacuo. The residue was taken up in MDC, washed successively with 1M hydrochloric acid (×2), water and brine then dried (MgSO$_4$), filtered and evaporated. The crude product was chromatographed on silica gel and the product triturated with ether to give a solid (2) (35 mg). $[\alpha]_D^{21}$ −84.7 (c 1.0 in CHCl$_3$);

$\nu_{max}$. (CHCl$_3$) 1785, 1715, 1690 cm$^{-1}$, δ ppm (CDCl$_3$) 1.53 (9H, s), 3.08 and 3.42 (2H, ABq, J 19 Hz), 3.40 and 3.67 (2H, ABq, J 15 Hz), 4.11 (3H, s), 5.08 (1H, d, J 4 Hz), 5.95 (1H, dd, J 4 and J 8 Hz), 6.83 (1H, s), 7.10 (1H, d, J 8 Hz), 7.2–7.4 (17H, m), 8.03 (2H, d, J 8 Hz).

EXAMPLE 2

(6R,7R)-3-(4-Carboxybenzyl)-7-[2,Z-methoxyimino-2-(2-aminothiazol-4-yl)-acetamido]ceph-3-em-4-carboxylic acid trifluoroacetic acid salt (3)

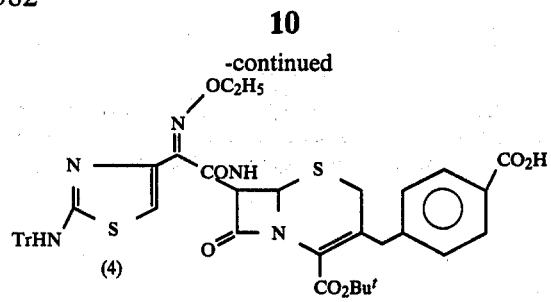

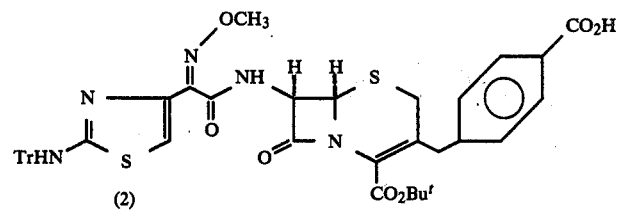

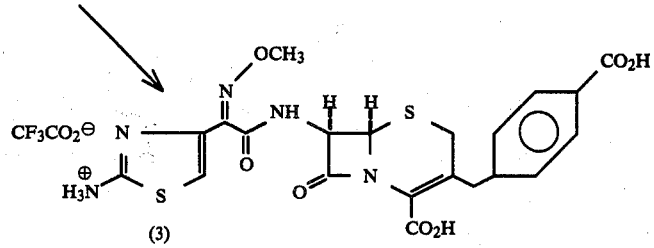

(6R,7R) t-Butyl 3-(4-carboxybenzyl)-7-[2,Z-methoxyimino-2-(2-triphenylmethylaminothiazol-4yl) acetamido]-ceph-3-em-4-carboxylate (2; 142 mg. 0.17 mmol) was treated with trifluoroacetic acid (TFA) at room temperature for 1 hour. The solvent was evaporated, toluene added and evaporated. This was repeated twice more. The residue was triturated with ether (×2) and dried in vacuo to yield (3) (108 mg) [α]$_D^{20}$ −25.4 (c 0.6 in TFA); λ$_{max}$. (EtOH) 237 n.m. (ε30, 175); $\nu_{max}$ (KBr) 1775 (br), 1675 (br) cm$^{-1}$; δ ppm (d$^6$-DMSO) inter alia 3.87 (3H, s), 5.18 (1H, d, J 4 Hz), 5.74 (1H, dd, J 4 and 8 Hz, collapses to doublet J 4 Hz on exchange), 6.78 (1H, s), 7.40 (2H, d, J 8 Hz), 7.90 (2H, d, J 8 Hz), 9.65 (1H, d, J 8 Hz, exch. D$_2$O).

EXAMPLE 3

(6R,7R) t-Butyl 3-(4-carboxybenzyl)-7-[2,Z-ethoxyimino-2-(2-triphenylmethylaminothiazol-4-yl)acetamido]-ceph-3-em-4-carboxylate (4)

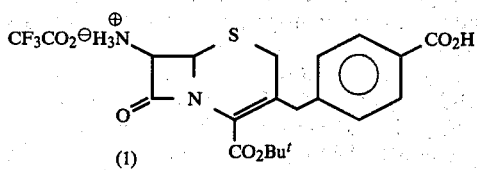

2,Z-Ethoxyimino-2-(2-triphenylmethylaminothiazol-4-yl)acetic acid (179 mg; 0.39 mmol) in dry MDC (5 ml) was cooled to −19° C. and treated with triethylamine (40 mg; 0.39 mmol) followed by phosphorus pentachloride (81 mg; 0.39 mmol). The mixture was stirred for 1 hour. The solvent was evaporated off and the residue taken up in dry MDC (5 ml). The solution added to a solution of (6R,7R) t-butyl 3-(4-carboxybenzyl)-7-aminoceph-3-em-4 carboxylate trifluoroacetic acid salt (1; 263 mg) in dry THF (5 ml) containing triethylamine (120 mg, 1.17 mmol) cooled to −10° C. After 15 minutes the mixture was allowed to warm to room temperature and stirred for a further 1.5 h. The solvent was evaporated off and the residue taken up in ethyl acetate, washed successively with dilute citric acid, water and brine, then dried and evaporated. Chromatography of the residue on silica gel (4 g) yielded a solid which was triturated with ether giving the product (4: 122 mg).

[α]$_D^{20°}$ −57.9 (c=1.9, CHCl$_3$); $\nu_{max}$. (CHCl$_3$) 1785, 1710, 1690 cm$^{-1}$; δ ppm (CDCl$_3$) 1.36 (3H, t, J 7.0 Hz), 1.53 (9H, s), 3.08 and 3.42 (2H, ABq, J 18.4 Hz), 3.36 and 4.29 (2H, ABq, J 15.3 Hz) 4.39 (2H, q, J 7.0 Hz), 5.10 (1H, d, J 4.7 Hz), 5.96 (1H, dd, J 4.7 and 9.4 Hz), 6.88 (1H, s), 7.22 (1H, d, J 9.4 Hz), 7.25 to 8.05 (aromatic H's).

EXAMPLE 4

(6R,7R)-3-(4-Carboxybenzyl)-7-[2,Z-ethoxyimino-2-(2-aminothiazol-4-yl)-acetamido]-ceph-3-em-4-carboxylic acid trifluoroacetic acid salt (5)

EXAMPLE 5

(6R,7R) t-Butyl 3-(4-[4'-methoxybenzyloxycarbonyl]benzyl)-7-[2,Z-(2-t-butoxycarbonylprop-2-oxymino)-2-(2-triphenylmethylaminothiazol-4-yl)acetamido]-ceph-3-em-4-carboxylate (7)

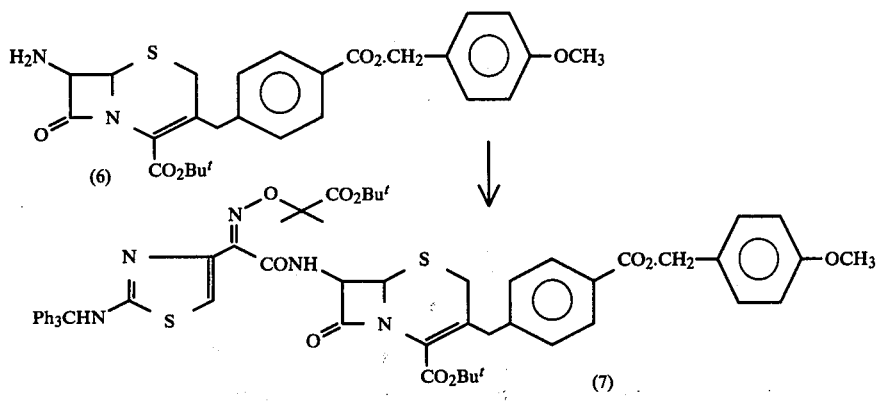

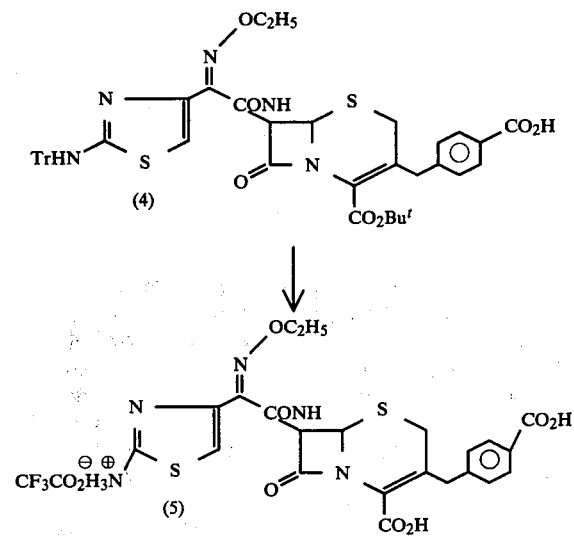

(6R,7R) t-Butyl 3-(4-carboxybenzyl)-7-[2,Z-ethoxyimino-2-(2-triphenylmethylaminothiazol-4-yl)acetamido]-ceph-3-em-4-carboxylate (4: 102 mg) was treated with TFA at room temperature for 1 h. The mixture was evaporated, toluene was added and the mixture evaporated; this was repeated once more. The residue was triturated with ether (×3), leaving the product (5; 57 mg).

$[\alpha]_D^{21}$ −30.8 (c=1.3, TFA); $\lambda_{max.}$ (EtOH) 237 n.m. ($\epsilon$29,715); $\nu_{max.}$ (KBr) 1765, 1655 (br.) cm$^{-1}$; δ ppm (d$^6$-DMSO) 1.20 (3H, t, J 7.0 Hz), 3.18 and 3.52 (2H, ABq, J 18.5 Hz), 3.68 and 3.99 (2H, ABq, J 14.6 Hz), 4.09 (2H, q, J 7.0 Hz), 519 (1H, d, J 4.7), 5.75 (1H, dd, J 4.7 and 8 Hz, collapsing to d, J 4.7 Hz on deuterium exchange), 6.74 (1H, s), 7.39 (2H, d, J 7.7 Hz), 7.89 (2H, d, J 7.7 Hz), 9.60 (1H, d, J 8.0 Hz).

A solution of (6R,7R)-t-butyl 3-[4'-methoxybenzyloxycarbonyl)benzyl]-7-aminoceph-3-em-4-carboxylate (6) (146 gm; 0.29 mmol) in dimethylformamide (DMF) (5 ml) containing (Z)-2-(2-t-butoxycarbonylprop-2-oximino)-2-(2-triphenylmethylaminothiazol-4-yl) acetic acid (166 mg; 0.29 mmol) was cooled to 0° C. and 1-hydroxybenzotriazole monohydrate (43 mg; 0.32 mmol) added followed by dicyclohexylcarbodiimide (DCCI) (66 mg; 0.32 mmol). The solution was allowed to warm to room temperature and stirred for 6.5 hours. The mixture was filtered, washing the dicylohexyl urea (DCU) with ether. The filtrate was diluted with water (50 ml) and extracted with ethyl acetate (×3). The combined extracts were washed with water, dilute hydrochloric acid, saturated sodium hydrogen carbonate solution, water and brine (brine was added to aid separation during the washings when necessary). The organic phase was dried, filtered and evaporated. The residue was chromatographed on silica gel to yield the product (7), 219 mg (71%) $[\alpha]_D^{24}$−34.3 (c=11.8, CHCl$_3$); $\lambda_{max.}$ (EtOH) 226 n.m. ($\epsilon$ 46,380); $\nu_{max.}$ (CHCl$_3$) 3390, 1785, 1715 and 1680 (sh) cm$^{-1}$; δ ppm (CDCl$_3$) (250 MHz) 1.39 (s, 9H), 1.59 and 1.61 (both s, together 6H), 1.81 (br.s, 1H), 3.02 and 3.34 (ABq, 2H, J 18 Hz), 3.51 and 4.12 (ABq, 2H, J 15 Hz), 3.81 (s, 3H), 5.04 (d, 1H, J 4.7 Hz), 5.29 (s, 2H), 5.97 (dd, 1H, J 9.0 and 4.7 Hz), 6.71 (s, 1H), 6.8 to 8.0 (m, 23H) and 8.09 (d, 1H, J 9.0 Hz).

EXAMPLE 6

(6R,7R)-3-(4-Carboxybenzyl)-7-[2,Z-(2-carboxyprop-2-oxyimino)-2-(2-aminothiazol-4-yl)-acetamido]-ceph-3-em-4-carboxylic acid trifluoroacetic acid salt (8)

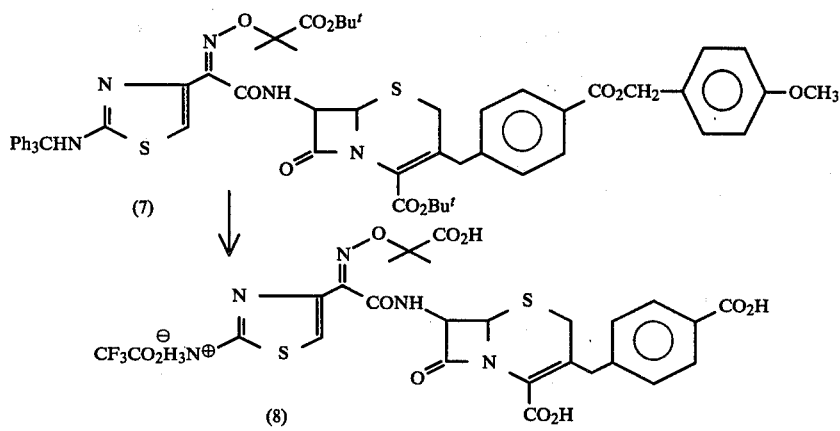

(6R7R)-t-Butyl 3-(4-(4'-methoxybenzyloxycarbonyl)-benzyl)-7-[2,Z-(2-t-butoxycarbonylprop-2-oximino)-2-(2-triphenylmethylaminothiazol-4-yl)acetamido]-ceph-3-em-4-carboxylate (7) (145 mg; 0.136 mmol) in anisole (4 ml) was treated with TFA (4 ml) at 0° C., then stirred at room temperature for 2.5 h. The mixture was evaporated. Toluene was added to the residue and the mixture was evaporated; this was repeated twice before drying thoroughly in vacuo. The solid was triturated with anhydrous ether and the product (8) filtered off, washing with more ether, to yield 76 mg (52%) $[\alpha]_D^{20}$ —40.5 (c=13.9, DMSO), $\lambda_{max}$. (EtOH) 237 n.m. ($\epsilon_m$ 32,496); $\nu_{max}$. (KRr), 3370 br, 1770, 1675 cm$^{-1}$; $\delta$ ppm [(CD$_3$)$_2$SO] (250 MHz) 1.42 and 1.43 (both s, together 6H), 3.17 and 3.52 (ABq, 2H, J 21.0 Hz), 3.65 and 4.04 (ABq, 2H, J 16.8 Hz) 5.20 (d, 1H, J 4.7 Hz), 5.80 (dd, 1H, J 8.6 and 4.7 Hz, collapses to d, J 4.7 Hz on exch.), 6.72 (s, 1H), 7.38 (d, 2H, J 8.4 Hz), 7.90 (d, 2H, J 8.4 Hz) and 9.46 (d, 1H, J 8.6 Hz, exch. D$_2$O).

DEMONSTRATION OF EFFECTIVENESS

TABLE 1

The minimum inhibitory concentrations (MIC) of the compound of Examples 2 and 4 found necessary to prevent growth of various bacteria in nutrient broth were as follows:-

| Bacterium | M.I.C. (μg/ml) Example 2 | Example 4 |
|---|---|---|
| Citrobacter freundii E 8 | 25 | 100 |
| Enterobacter cloacae N 1 | 3.1 | 50 |
| Escherichia coli 0111 | 6.2 | 3.1 |
| Escherichia coli JT 39 (R+) | 6.2 | 1.6 |
| Klebsiella aerogenes A | 0.2 | 0.1 |
| Proteus mirabilis 977 | 0.8 | 0.2 |
| Proteus morganii I 580 | 1.6 | 100 |
| Proteus rettgeri WM 16 | 12.5 | 100 |
| Proteus vulgaris W 091 | 12.5 | 3.1 |
| Pseudomonas aeruginosa A | >100 | >100 |
| Salmonella typhimurium CT 10 | 0.4 | 0.8 |
| Serratia marcescens US 20 | 12.5 | 3.1 |
| Shigella sonnei MB 11967 | 0.4 | 0.8 |
| Bacillus subtilis A | 25 | 12.5 |
| Staphylococcus aureus Oxford | 12.5 | 3.1 |
| Staphylococcus aureus Russell | 12.5 | 6.2 |
| Streptococcus faecalis I | >100 | >100 |
| Streptococcus pneumoniae CN 33 | ≦0.1 | 6.2 |
| Streptococcus pyogenes CN 10 | ≦0.1 | — |

TABLE 2

The Minimum Inhibitory concentrations (MIC) of the compound of Example 6 found necessary to prevent growth of various bacteria on agar were as follows:

| Bacterium | MIC (μg/ml) |
|---|---|
| Escherichia coli JT4 | 2.5 |
| Escherichia coli JT425 | 25 |
| Pseudomonas aeruginosa NCTC 10662 | 5 |
| Pseudomonas aeruginosa Dalgleish | 2.5 |
| Serratia marcescens US32 | 2.5 |
| Klebsiella aerogenes A | 0.2 |
| Enterobacter cloacae N1 | 1.0 |
| Proteus mirabilis C977 | 0.05 |
| Proteus morganii | 2.5 |
| Proteus rettgeri | 0.2 |
| Bacillus subtilis | >100 |
| Staphylococcus aureus Oxford | 100 |
| Staphylococcus aureus Russell | >100 |
| Streptococcus faecalis I | >100 |
| Streptococcus pyogenes CN10 | 2.5 |
| Neisseria catarrhalis 1502 | <0.02 |

What I claim is:

1. A compound of the formula (I):

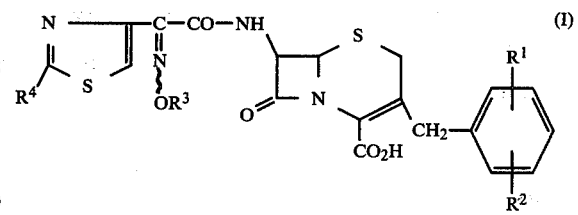

a pharmaceutically acceptable salt thereof or in-vivo hydrolyzable ester of any carboxy group, wherein R$^1$ is carboxy, R$^2$ is hydrogen or carboxy, R$^3$ is hydrogen, alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, alkyl of 1 to 6 carbon atoms, alkenyl of 2 to 6 carbon atoms or said alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P-(=O)O— wherein each alkoxy moiety has from 1 to 6 carbon atoms, alkyl or alkenyl substituted by chloro, bromo, fluoro, hydroxy, carboxy, alkoxy of 1 to 6 carbon atoms, phenyl, naphthyl, thienyl, pyridyl, pyrrolyl, indolyl or furyl, or said alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms substituted by alkyl of 1 to 6 carbon atoms, or said alkyl being substituted by alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, and $R^4$ is an amino or protected amino group.

2. A compound according to claim 1 wherein $R^2$ is hydrogen.

3. A compound according to claim 1 or claim 2 wherein $R^1$ is a carboxy group located in the para-position of the phenyl ring.

4. A compound according to claim 1 wherein $R^3$ is hydrogen, methyl, ethyl, propyl, butyl, formyl, acetyl, methoxycarbonyl, ethenyl, methanesulphonyl, carboxymethyl, carboxyethyl or 2-carboxyprop-2-yl.

5. A compound according to claim 1.

6. A compound according to claim 1 when in the syn-form (II):

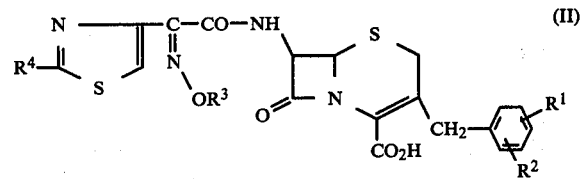

7. A compound according to claim 1 which is of the formula (VI):

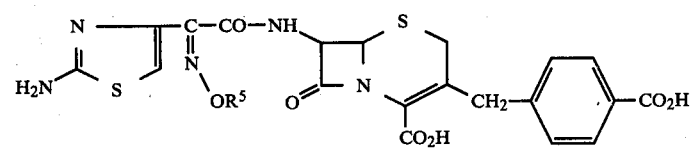

or a pharmaceutically acceptable salt thereof wherein $R^5$ is hydrogen or alkyl of 1 to 4 carbon atoms unsubstituted or substituted by carboxy.

8. A compound according to claim 1 selected from:
(6R,7R)-3-(4-carboxybenzyl-7-[2,Z-methoxyimino-2-(2-aminothiazol-4-yl)-acetamido]-ceph-3-em-4-carboxylic acid,
(6R,7R)-3-(4-carboxybenzyl)-7-[2-Z-ethoxyimino-2-(2-aminothiazol-4-yl)-acetamido]-ceph-3-em-4-carboxylic acid, and
(6R,7R)-3-(4-carboxybenzyl)-7-[2,Z-(2-carboxyprop-2-oxyimino)-2-(2-aminothiazol-4-yl)-acetamido]-ceph-3-em-4-carboxylic acid.

9. A pharmaceutical composition useful for treating bacterial infections in mammals including humans which comprises an antibacterially effective amount of a compound of the formula (I):

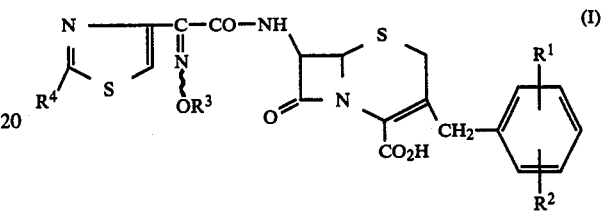

a pharmaceutically acceptable salt thereof or in-vivo hydrolyzable ester of any carboxy group, wherein $R^1$ is carboxy, $R^2$ is hydrogen or carboxy, $R^3$ is hydrogen, alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, alkyl of 1 to 6 carbon atoms, alkenyl of 2 to 6 carbon atoms or said alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, alkyl or alkenyl substituted by chloro, bromo, fluoro, hydroxy, carboxy, alkoxy of 1 to 6 carbon atoms, phenyl, naphthyl, thienyl, pyridyl, pyrrolyl, indolyl or furyl, or said alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoycarbamoyl of 1 to 6 carbon atoms and dialkoxy-P(=O)O— wherein each alkoxy moiety has from 1 to 6 carbon atoms substituted by alkyl of 1 to 6 carbon atoms, or said alkyl being substituted by alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety had from 1 to 6 carbon atoms, and $R^4$ is an amino or protected amino group, in combination with a pharmaceutically acceptable carrier.

10. A method of treating bacterial infections in mammals including humans which comprises administering to such a mammal in need thereof an antibacterially effective amount of a compound of the formula (I):

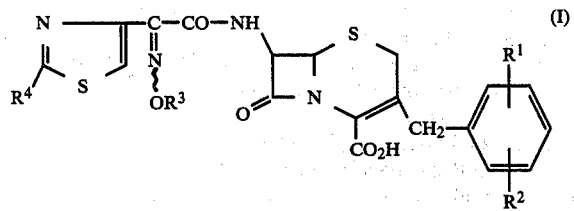

a pharmaceutically acceptable salt thereof or in-vivo hydrolyzable ester of any carboxy group, wherein $R^1$ is carboxy, $R^2$ is hydrogen or carboxy, $R^3$ is hydrogen, alkanoyl of 1 of 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, alkyl of 1 to 6 carbon atoms, alkenyl of 2 to 6 carbon atoms or said alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, alkyl or alkenyl substituted by chloro, bromo, fluoro, hydroxy, carboxy, alkoxy of 1 to 6 carbon atoms, phenyl, naphthyl, thienyl, pyridyl, pyrrolyl, indolyl or furyl, or said alkanoyl of 1 to 6 carbon atoms, alkoxycarbonyl of 1 to 6 carbon atoms, benzoyl, naphthoyl, phenylalkanoyl of 1 to 6 carbon atoms in the alkyl moiety, phenylalkoxycarbonyl of 1 to 6 carbon atoms in the alkoxy moiety, alkanesulphonyl of 1 to 6 carbon atoms, benzenesulphonyl, toluenesulphonyl, alkylcarbamoyl of 1 to 6 carbon atoms, phenylcarbamoyl, phenylalkylcarbamoyl of 1 to 6 carbon atoms in the alkyl moiety, alkanoylcarbamoyl of 1 to 6 carbon atoms and dialkoxy-P(=O)O— wherein each alkoxy moiety has from 1 to 6 carbon atoms, and $R^4$ is an amino or protected amino group, in combination with a pharmaceutically acceptable carrier.

11. A composition according to claim 9 wherein $R^2$ is hydrogen.

12. A composition according to claim 9 wherein $R^1$ is a carboxy group located in the para-position of the phenyl ring.

13. A composition according to claim 9 wherein $R^3$ is hydrogen, methyl, ethyl, propyl, butyl, formyl, acetyl, methoxycarbonyl, ethenyl, methanesulphonyl, carboxymethyl, carboxyethyl or 2-carboxyprop-2-yl.

14. A composition according to claim 9 wherein $R^4$ is amino.

15. A composition according to claim 9 when the compound is in the syn-form (II):

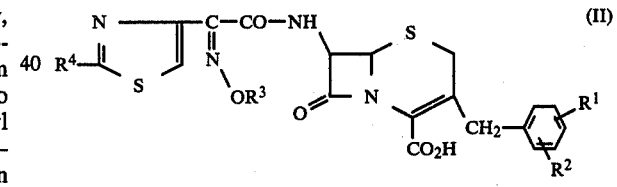

16. A composition according to claim 9 wherein the compound is of the formula (VI):

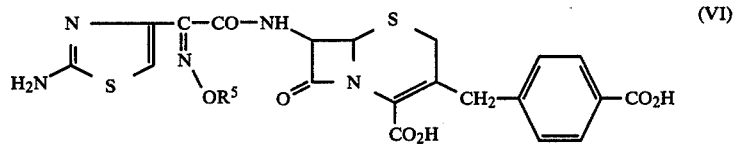

or a pharmaceutically acceptable salt thereof wherein $R^5$ is hydrogen or alkyl of 1 to 4 carbon atoms unsubstituted or substituted by carboxy.

17. A composition according to claim 9 wherein the compound is selected from:
(6R,7R)-3-(4-carboxybenzyl)-7-[2,Z-methoxyimino-2-(2-aminothiazol-4-yl)-acetamido]-ceph-3-em-4-carboxylic acid,
(6R,7R)-3-(4-carboxybenzyl)-7-[2-Z-ethoxyimino-2-(2-aminothiazol-4-yl)-acetamido]-ceph-3-em-4-carboxylic acid, and (6R,7R)-3-(4-carboxybenzyl)-7-[2,Z-(2-carboxyprop-2-oxyimino)-2-(2-aminothiazol-4-yl)-acetamido]-ceph-3-em-4-carboxylic acid.

18. A method according to claim 10 wherein $R^2$ is hydrogen.

19. A method according to claim 10 wherein $R^1$ is a carboxy group located in the para-position of the phenyl ring.

20. A method according to claim 10 wherein $R^3$ is hydrogen, methyl, ethyl, propyl, butyl, formyl, acetyl, methoxycarbonyl, ethenyl, methanesulphonyl, carboxymethyl, carboxyethyl or 2-carboxy-prop-2-yl.

21. A method according to claim 10 wherein $R^4$ is amino.

22. A method according to claim 10 wherein the compound is in the syn-form (II):

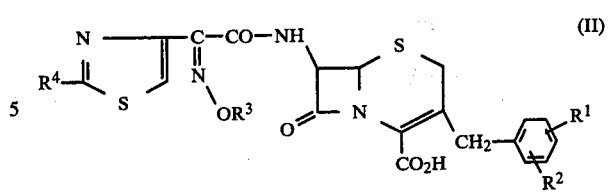

23. A method according to claim 10 wherein the compound is of the formula (VI):

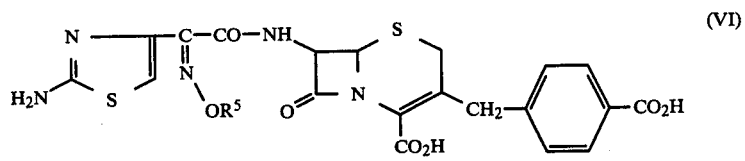

or a pharmaceutically acceptable salt thereof wherein $R^5$ is hydrogen or alkyl of 1 to 4 carbon atoms unsubstituted or substituted by carboxy.

24. A method according to claim 10 wherein the compound is selected from:

(6R,7R)-3-(4-carboxybenzyl)-7-[2,Z-methoxyimino-2-(2-aminothiazol-4-yl)-acetamido]-ceph-3-em-4-carboxylic acid, (6R,7R)-3-(4-carboxybenzyl)-7-[2-Z-ethoxyimino-2-(2-aminothiazol-4-yl)-acetamido]-ceph-3-em-4-carboxylic acid, and (6R,7R)-3-(4-carboxybenzyl)-7-[2,Z-(2-carboxyprop-2-oxyimino)-2-(2-aminothiazol-4-yl)-acetamido]-ceph-3-em-4-carboxylic acid.

* * * * *